United States Patent [19]

Sakurai et al.

[11] 4,044,601
[45] Aug. 30, 1977

[54] SMOKE AND GAS SENSOR ELEMENT
[75] Inventors: Yo Sakurai, Kunitachi; Hidehito Obayashi; Tetsuo Gejyo, both of Tokyo, all of Japan
[73] Assignee: Hitachi, Ltd., Japan
[21] Appl. No.: 600,052
[22] Filed: July 29, 1975
[30] Foreign Application Priority Data
July 29, 1974 Japan .................................. 49-86095
[51] Int. Cl.$^2$ ............................................ G01N 27/12
[52] U.S. Cl. .................................... 73/23; 23/254 E; 338/34
[58] Field of Search ............. 73/23, 27 R; 324/71 SN; 338/34; 348/237 R; 23/232 E, 254 E
[56] References Cited
U.S. PATENT DOCUMENTS
3,695,848 10/1972 Taguchi ................... 73/27 R
3,865,550 2/1975 Bott et al. ................ 73/23
3,951,603 4/1976 Obayashi et al. ........ 73/27 R Primary Examiner—Richard C. Queisser
Assistant Examiner—Stephen A. Kreitman
Attorney, Agent, or Firm—Craig & Antonelli

[57] ABSTRACT

A sensor element for detecting smoke and/or reducing gases, which comprises a shaped body formed from a material consisting essentially of:

A. a complex metal oxide having a perovskite type crystal structure and represented by the general formula $ABO_3 - \delta$ wherein A is at least one element selected from the group consisting of yttrium, a rare earth element having an atomic number of from 57 to 71 and an alkaline earth metal, B is at least one element selected from the group consisting of transition metals having atomic numbers from 21 to 30, O is oxygen and $\delta$ is a nonstoichiometric parameter which may vary from 0 to 0.25 and B. at least one metal oxide selected from the group consisting of CdO, $In_2O_3$, SnO, $Tl_2O_3$ and PbO.

22 Claims, 2 Drawing Figures

SMOKE AND GAS SENSOR ELEMENT

BACKGROUND OF THE INVENTION

This invention relates to a sensor element for detecting trace amounts of smoke and/or gaseous reducing substances contained in the atmosphere, exhaust gases, etc.

For detecting these trace amounts of smoke and/or reducing gases, there are such conventionally known methods as gas chromatography and a method which makes use of a semiconductor element. Gas chromatography, however, cannot be said to be a convenient and inexpensive detecting method because it requires a large-scale apparatus and a certain degree of skill in the analytical procedure.

Among the detecting methods which make use of a semiconductor element for the sensor, there is known, for example, a method which utilizes the change in the specific resistance of a shaped piece comprising stannic oxide as the main constituent. This method, however, has the disadvantages that the sensor has an extremely large temperature coefficient of resistance (from $2.5 \times 10^6 \, \Omega$ at 25° C. to $10^4 \, \Omega$ at 250° C. in air), and, in addition, the resistance of the sensor changes with changing water vapor content.

SUMMARY OF THE INVENTION

This invention relates to an improvement in a sensor element for detecting trace amounts of smoke and/or gaseous reducing substances such as alcohols, aldehydes, hydrocarbons, carboxylic acids, ketones, esters, nitrogen oxides and carbon monoxide in the atmosphere, exhaust gases, etc. and to the sensor devices employing such elements.

An earlier application of H. Obayashi and T. Gejyo, both of the present invention, Ser. No. 47-68308, filed in Japan July 8, 1972 (corresponding to U.S. application Ser. No. 376,276 in the United States, filed July 5, 1973), now U.S. Pat. No. 3,951,603, and entitled "Gas-sensor Element and Method for Detecting Reducing Gas or Oxygen Gas" discloses a gas-sensor element employing a complex metal oxide having a perovskite-type crystal structure.

The present invention relates to an improvement of the above-mentioned sensor-element.

DESCRIPTION OF THE PREFERRED EMBODIMENTS

Figure 1:
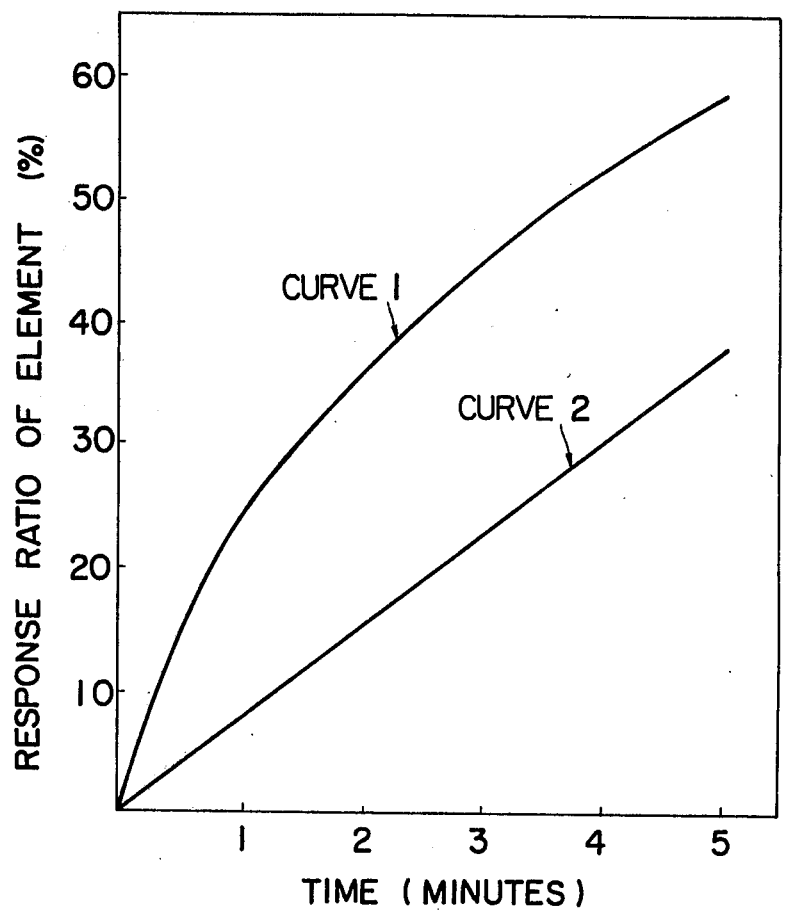
FIG. 1 is the response ratio of the element against time when the element is placed in contact with a 10% concentration of smoke.

The sensor element of the present invention comprises a layer or shaped body of an admixture of (1), a complex metal oxide having a perovskite type crystal structure and represented by the general formula $ABO_{3-\delta}$, wherein A is at least one element selected from the group consisting of yttrium, a rare earth element of an atomic number from 57 to 71 and an alkaline earth metal, B is at least one element selected from the group consisting of transition metals of the atomic numbers from 21 to 30, O is oxygen and $\delta$ is a nonstoichiometric parameter ranging from 0 to 0.25, (hereafter the number of oxygen atoms in the formula is expressed as 3, $\delta$ being omitted from the expression), and (2), at least one metal oxide selected from the group consisting of $CdO$, $In_2O_3$, $SnO$, $Tl_2O_3$ and $PbO$. Particle size of each oxide is preferably 0.05 to 2 microns, but other size may be used.

The above metal oxides (2) are effective at between from 5% and 50% by weight, based on the weight of the complex metal oxide (1), and more effective at between from 5% and 30% by weight of the complex metal oxide within the total composition forming the sensor element.

The response time of the above-mentioned sensor element is shorter than that of an element which has no metal oxide when these elements are placed in contact with smoke or gas. Accordingly, this gas-sensor is suitable for use as an alarm.

The working temperature of the above element should preferably be at about 100° to 500° C. and more preferably 180° to 400° C.

The present invention is illustrated below in further detail with reference to several examples; however, these examples are intended to illustrate the invention and should not be construed so as to limit the scope of the invention.

EXAMPLE 1

One part by weight of a powdered complex metal oxide, $LaNiO_3$, and 5% by weight of powdered $In_2O_3$, based on the weight of the complex metal oxide, were mixed with ethanol and dried. This mixture was mixed again with about 1 part by weight of a 1% by weight, butyl acetate solution of a nitrocellulose binder to form a slurry. The slurry was coated on an alumina base-plate to cover an area measuring 1 mm. wide by 5 mm. long, with thickness of 20 $\mu$m. Then, this coating was sintered at 1000° C. for 1 hour to obtain a sensor element; generally sintering is from 800° to 1000° C. at 0.5 to several hours.

The electrical resistance of this element was 95 $\Omega$, 88 $\Omega$ and 85 $\Omega$ at 95° C., 250° C. and 300° C., respectively. In other words, the temperature coefficient of resistance of the element is small.

In FIG. 1, curve 1 shows the response ratio of the element (percentage of the change in resistances of the element) with time when the element is placed in contact with a 10% concentration of smoke (a 10% attenuation of light per 1 m of smoke, based on the smoke from a scrolled joss stick). Smoke which is obtained from the wood is as follows at dry distillation:

| | |
|---|---|
| carbon | about 38% |
| liquid (acetic acid, methyl alcohol, acetone, aldehyde, tar and methyl acetate, etc.) | about 24% |
| gases ($CO_2$, CO, $CH_4$, $C_2H_2$ and $C_2H_4$, etc.) | about 15% |
| $H_2O$ | about 23% |

Figure 2:
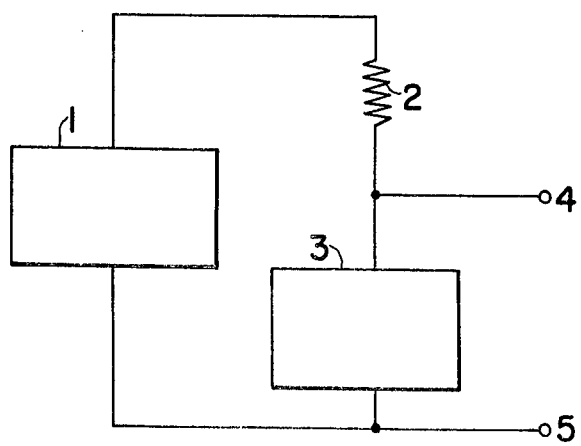
FIG. 2 is the electric circuit for the measurement of the change of resistance of the element.

The electric circuit for the above measurement is shown in FIG. 2. As is indicated in FIG. 2, a constant-voltage source of 1 of 0.2 V and a fixed resistance 2, of 100 $\Omega$ were employed to allow a small current (about 1 m A) to pass through the sensor element 3. The change (increase) in the terminal voltage of the sensor element, 3, caused by contact with the gas was measured with a voltmeter of high resistance input and a recorder connected to junctions 4 and 5. The data was measured at 250° C. In the following examples, the value of the fixed resistance is changed to keep it roughly equal to the resistance of the element. The current is maintained at about 1 mA by changing the voltage of the source.

As a comparative example, an element was prepared from only $LaNiO_3$ with no added $In_2O_3$.

In FIG. 1, curve 2 shows the response ratio of this element against time under the same conditions as above.

The response time of the element with added $In_2O_3$ is shorter than that of the element with no added $In_2O_3$ as is evident from FIG. 1.

EXAMPLES 2-10

Elements similar to that in Example 1 were prepared from $LaNiO_3$ with the additives shown in Table 1. The times for which the response ratio of these elements changed 10%, under the same conditions as in Example 1, are shown in Table 1.

Table 1

| Example No. | Additive | Quantities of the Additive (% by weight) based on weight of $LaNiO_3$ | Time (sec.) |
|---|---|---|---|
| comparative example | — | — | 80 |
| 2 | $In_2O_3$ | 5 | 18 |
| 3 | $In_2O_3$ | 10 | 15 |
| 4 | $In_2O_3$ | 20 | 10 |
| 5 | $In_2O_3$ | 30 | 7 |
| 6 | CdO | 10 | 20 |
| 7 | SnO | 10 | 20 |
| 8 | $Tl_2O_3$ | 20 | 15 |
| 9 | PbO | 20 | 10 |
| 10 | $In_2O_3$ + PbO 1:1 weight ratio | 30 | 10 |

EXAMPLES 11 to 25

Elements similar to that in Example 1 were prepared from the complex metal oxides with the additives shown in Tables 2 and 3. The times for which the response ratio of the elements changed 10%, under the same conditions as in Example 1, are shown in Tables 2 and 3.

Table 2

| Example No. | Complex Oxide | No Additive | Time (sec.) Additive 10% by wt. of $In_2O_3$ | 20% by wt. of SnO |
|---|---|---|---|---|
| 11 | $La_{0.5}Sr_{0.5}CoO_3$ | 100 | 20 | 20 |
| 12 | $Nd_{0.5}Sr_{0.5}CoO_3$ | 120 | 25 | 25 |
| 13 | $Sm_{0.5}Sr_{0.5}CoO_3$ | 120 | 20 | 20 |
| 14 | $Dy_{0.5}Sr_{0.5}CoO_3$ | 120 | 25 | 25 |
| 15 | $Er_{0.5}Sr_{0.5}CoO_3$ | 100 | 20 | 20 |
| 16 | $Sm_{0.5}Sr_{0.5}Co_{0.8}Fe_{0.2}O_3$ | 80 | 15 | 20 |
| 17 | $Sm_{0.5}Sr_{0.5}Co_{0.8}Mn_{0.2}O_3$ | 60 | 12 | 15 |
| 18 | $La_{0.5}Sr_{0.5}Fe_{0.8}Co_{0.2}O_3$ | 50 | 15 | 20 |
| 19 | $La_{0.99}Ca_{0.01}NiO_3$ | 130 | 30 | 40 |

Table 3

| Example No. | Complex Oxide | No Additive | 5.5% by wt. of $In_2O_3$ | 3% by wt. of $In_2O_3$ + 3% by wt. of SnO | 3% by wt. of PbO + 3% by wt. of $Tl_2O_3$ |
|---|---|---|---|---|---|
| 20 | $Y Co_{0.5}Fe_{0.5}O_3$ | 200 | 40 | 35 | 35 |
| 21 | $Y_{0.1}Sm_{0.4}Sr_{0.5}CoO_3$ | 120 | 20 | 18 | 18 |
| 22 | $Sm_{0.4}Gd_{0.1}Sr_{0.5}CoO_3$ | 130 | 20 | 18 | 18 |
| 23 | $Sm_{0.5}Sr_{0.5}Co_{0.7}Fe_{0.2}Ti_{0.1}O_3$ | 120 | 20 | 20 | 20 |
| 24 | $Sm_{0.5}Sr_{0.5}Co_{0.7}Fe_{0.2}V_{0.1}O_3$ | 120 | 20 | 20 | 20 |
| 25 | $SrCoO_3$ | 150 | 25 | 20 | 20 |

What is claimed is:

1. In a sensor device for detecting the presence of smoke and/or a gaseous substance in an atmosphere, said sensor device including a sensor element whose resistance changes with the presence of said smoke or gaseous substance, said sensor element having a surface capable of coming into contact with said atmosphere and a means for indicating the presence of said smoke or gaseous substance in said atmosphere in response to a change in the resistance of said sensor element, the improvement wherein said sensor element is formed from a material comprising:
   1. a complex metal oxide having a perovskite type crystal structure and represented by the general formula $ABO_{3-\delta}$, wherein A is at least one element selected from the group consisting of yttrium, a rare earth element of an atomic number from 57 to 71, and an alkaline earth metal, B is at least one element selected from the group consisting of transition metals of the atomic numbers from 21 to 30, O is oxygen and $\delta$ is a nonstoichiometric parameter, and
   2. at least one metal oxide selected from the group consisting of CdO, $In_2O_3$, SnO, $Tl_2O_3$ and PbO.

2. A sensor according to claim 1, wherein the complex metal oxide represented by the general formula $ABO_{3-\delta}$ contains at least lanthanum as A.

3. A sensor according to claim 1, wherein the complex metal oxide represented by the general formula $ABO_{3-\delta}$ contains at least strontium as A.

4. A sensor according to claim 1, wherein the complex metal oxide represented by the general formula $ABO_{3-\delta}$ contains at least nickel as B.

5. A sensor according to claim 1, wherein said sensor element is in the form of a plate, rod, cylinder or disc.

6. The sensor according to claim 1, wherein said material is a coating on a substrate.

7. A sensor according to claim 6, wherein said substrate is in the form of a plate, rod or cylinder.

8. The sensor according to claim 1, further comprising a means for keeping the temperature of said sensor element constant.

9. A sensor according to claim 1, wherein said metal oxide (2) is more than 5% and less than 50% by weight, based on the weight of the complex metal oxide (1).

10. A sensor according to claim 9, wherein said metal oxide (2) is more than 5% or less than 30% by weight, based on the weight of the complex metal oxide (1).

11. In a method for detecting the presence of smoke and/or a gaseous substance in an atmosphere, comprising bringing the atmosphere into contact with a sensor element, whose resistance changes with the presence of said smoke and/or gaseous substance, and measuring the resistance of said sensor element while said atmosphere is in contact therewith, the improvement wherein said sensor element is formed from a material comprising (1), a complex metal oxide having a perovskite type crystal structure and represented by the general formula $ABO_{3-\delta}$, wherein A is at least one element selected from the group consisting of yttrium, a rare earth element of an atomic number from 57 to 71 and an alkaline earth metal, B is at least one element selected from the group consisting of transition metals of the atomic numbers from 21 to 30, O is oxygen and $\delta$ is a nonstoichiometric parameter, and (2), at least one metal oxide selected from the group consisting of CdO, $In_2O_3$, SnO, $Tl_2O_3$ and PbO.

12. A method according to claim 11, wherein the smoke and/or the gaseous substance is brought in contact with said sensor element at a temperature of about 100° to 500° C.

13. A method according to claim 11, wherein the complex metal oxide represented by the general formula $ABO_{3-\delta}$ contains at least lanthanum as A.

14. A method according to claim 11, wherein the complex metal oxide represented by the general formula $ABO_{3-\delta}$ contains at least strontium as A.

15. A method according to claim 11, wherein the complex metal oxide represented by the general formula $ABO_{3-\delta}$ contains at least nickel as B.

16. A method according to claim 11, wherein said metal oxide (2) is more than 5% and less than 50% by weight, based on the weight of the complex metal oxide (1).

17. A method according to claim 11, wherein said metal oxide (2) is more than 5% and less than 30% by weight based on the weight of the complex metal oxide (1).

18. A method according to claim 11, wherein the gaseous substance is a reducing gas.

19. A method according to claim 11, wherein the sensing element is maintained at a consant temperature.

20. A sensor element for detecting smoke and/or reducing gases, which comprises a shaped body or layer formed from a material consisting essentially of a mixtue of:
A. a complex metal oxide having a perovskite type crystal structure and represented by the general formula $ABO_{3-\delta}$ wherein A is at least one element selected from the group consisting of yttrium, a rare earth element having an atomic number of from 57 to 71 and an alkaline earth metal, B is at least one element selected from the group consisting of transition metals having the atomic numbers from 21 to 30, O is oxygen and $\delta$ is a nonstoichiometric parameter which may vary from 0 to 0.25 and
B. at least one metal oxide selected from the group consisting of CdO, $In_2O_3$, SnO, $Tl_2O_3$ and PbO.

21. A sensor element according to claim 20, wherein the amount of said metal oxide (B) within said mixture is from 5% to 50% by weight, based on the weight of the complex metal oxide (A).

22. A sensor element according to claim 20, wherein the amount of said metal oxide (B) within said mixture is from 5% to 30% by weight, based on the weight of the complex metal oxide (A).

* * * * *